(12) United States Patent
Torgerson et al.

(10) Patent No.: US 10,317,420 B2
(45) Date of Patent: Jun. 11, 2019

(54) DETAILED ASSAY PROTOCOL SPECIFICATION

(71) Applicant: Luminex Corporation, Austin, TX (US)

(72) Inventors: David R. Torgerson, Round Rock, TX (US); Matthew S. Fisher, Austin, TX (US)

(73) Assignee: Luminex Corporation, Austin, TX (US)

( * ) Notice: Subject to any disclaimer, the term of this patent is extended or adjusted under 35 U.S.C. 154(b) by 109 days.

(21) Appl. No.: 14/964,022

(22) Filed: Dec. 9, 2015

(65) Prior Publication Data

US 2016/0169924 A1 Jun. 16, 2016

Related U.S. Application Data

(60) Provisional application No. 62/092,121, filed on Dec. 15, 2014.

(51) Int. Cl.
*G06F 19/00* (2018.01)
*G01N 35/00* (2006.01)
(Continued)

(52) U.S. Cl.
CPC ......... *G01N 35/0092* (2013.01); *G16H 40/60* (2018.01); *C12Q 1/686* (2013.01);
(Continued)

(58) Field of Classification Search
CPC .......... G06F 19/24; G06F 19/18; G06F 19/20; G06F 19/22; G06F 19/366;
(Continued)

(56) References Cited

U.S. PATENT DOCUMENTS 5,499,188 A * 3/1996 Kline, Jr. ............... G05B 15/02
700/106
8,770,471 B2 7/2014 Cong et al.
(Continued)

FOREIGN PATENT DOCUMENTS

| WO | 2013/049782 | 4/2013 |
| WO | 2015/021460 | 2/2015 |
| WO | 2016/025452 | 2/2016 |

OTHER PUBLICATIONS

International Search Report and Written Opinion in PCT Application No. PCT/US2015/064810 dated Feb. 12, 2016, 13 pages.
(Continued)

*Primary Examiner* — Mary K Zeman
(74) *Attorney, Agent, or Firm* — Meyertons, Hood, Kivlin, Kowert & Goetzel, P.C.

(57) ABSTRACT

Techniques are disclosed relating to assay configuration. Assay devices are often used to determine characteristics of test samples, e.g., using polymerase chain reaction (PCR) or Deoxyribonucleic Acid (DNA) melt techniques. Various disclosed techniques allow detailed specification of assay parameters. This may allow user modification of assays and/or assay development by third parties. In embodiments in which assay parameters are specified using a separate device, these techniques may reduce validation requirements resulting from modified assays. In some embodiments, assay configuration information that may be added/removed/modified may include: a sequence of operations, parameters for the sequence of operations, data processing parameters, call logic rules/dependencies, and/or reporting rules.

10 Claims, 12 Drawing Sheets

1100

Cause a user configuration tool for an assaying device to be displayed
1110

Generate, based on user input to the user configuration tool, first configuration information that specifies a sequence of operations for an assay and a set of parameters for the sequence of operations
1120

Generate, based on user input to the user configuration tool, second configuration information that specifies a set of rules for selection of an outcome from among a plurality of outcomes of the assay, where the user input specifies at least one new rule of the set of rules
1130

(51) Int. Cl.
*G16H 40/60* (2018.01)
*C12Q 1/686* (2018.01)

(52) U.S. Cl.
CPC ............... *G01N 2035/0094* (2013.01); *G01N 2035/0096* (2013.01); *G01N 2035/00891* (2013.01)

(58) Field of Classification Search
CPC .... G06F 19/3437; G06F 19/345; G06F 19/00; G06F 19/12; G06F 19/28; G06F 19/26; G06F 19/16; G06F 19/708; G06F 19/709; G06F 19/325; G01N 21/6428; G01N 33/582; G01N 2030/8804; G01N 21/64; G01N 21/6486; G01N 21/76; G01N 21/763; C12Q 1/6869; C12Q 2565/629; C12Q 2600/156; C12Q 2600/158; C12Q 1/6827; C12Q 1/686; C12Q 1/6883; C12Q 2535/122; C12Q 2563/159; C12Q 1/06; C12Q 1/6809; C12Q 2537/16; C12Q 2537/165; C12Q 2600/112; C12Q 2600/118; C12Q 1/6851; C12Q 1/6881; C12Q 1/689; C12Q 2525/151; C12Q 2531/113; C12Q 1/6876; G16H 10/40; G16H 50/20; G16H 50/50; G06N 20/00; G06N 7/005; G06Q 10/00; G06Q 30/0621; G06Q 30/0633; G06Q 30/0641; G06Q 50/22
See application file for complete search history.

(56) References Cited

U.S. PATENT DOCUMENTS

| | | | | |
|---|---|---|---|---|
| 8,850,424 | B2 * | 9/2014 | Friedman | G06F 8/61 717/170 |
| 9,114,398 | B2 * | 8/2015 | Knight | B01L 3/5027 |
| 2008/0261220 | A1 * | 10/2008 | Cracauer | C12P 19/34 435/6.11 |
| 2009/0089174 | A1 * | 4/2009 | Brunner | G06Q 30/0621 705/26.5 |
| 2010/0252123 | A1 | 10/2010 | Mathies et al. | |
| 2011/0059861 | A1 | 3/2011 | Nolan et al. | |
| 2012/0303472 | A1 | 11/2012 | Koehler et al. | |
| 2013/0331286 | A1 | 12/2013 | Sappenfield | |
| 2014/0040058 | A1 | 2/2014 | Aklian | |
| 2014/0051590 | A1 | 2/2014 | Wu et al. | |
| 2014/0211204 | A1 * | 7/2014 | Stedtfeld | G01N 21/6486 356/244 |
| 2014/0234949 | A1 * | 8/2014 | Wasson | G01N 35/1065 435/287.2 |

OTHER PUBLICATIONS

European Search Report in Appl. No. 15870721.6 dated Aug. 17, 2018, 13 pages.

* cited by examiner

FIG. 3

ASSAY SETTINGS

| Assay Name | HSV |
| --- | --- |
| Assay Type | IVD |
| Starter Assay | ☐ |

| Description | (optional) |
| --- | --- |

| Channel | Dye | Associated Tests |
| --- | --- | --- |
| 1 | - | |
| 2 | 6FAM ▽ | HSV |
| 3 | - | |
| 4 | AP559 ▽ | [SPC] |
| 5 | - | |
| 6 | AP662 ▽ | [MC] |

THERMAL PARAMETERS

| Sample Prep Step Enabled | ☑ |
|---|---|

| Pre-PCR | |
|---|---|
| Pre-Heat Temperature (C) | 50 |
| Pre-Heat Hold Time (sec) | 420 |
| Activation Temperature (C) | 95 |
| Activation Time (sec) | 120 |

| PCR | |
|---|---|
| RT-PCR Step Enabled | ☑ |
| Number of PCR Steps | 2 |
| Optical Read Location | Anneal |
| Number of PCR Cycles | 45 |
| Denature Temperature (C) | 95 |
| Denature Time (sec) | 5 |
| Anneal Temperature (C) | 58 |
| Anneal Hold Time (sec) | 7 |

| Melt | |
|---|---|
| Melt Step Enabled | ☑ |
| Melt Start Temperature (C) | 60 |
| Melt Final Temperature (C) | 95 |
| Melt Temperature Step (C) | 0.5 |
| Melt Hold Time (sec) | 2 |

FIG. 5

ANALYSIS PARAMETERS

| Wavelength Channel | |
|---|---|
| AP662 | ▽ |

| PCR Data Reduction Parameters | |
|---|---|
| Slope Norm Target | 0.3 |
| Number of Smoothing Points | 11 |
| Is Quenching | ☑ |
| Verbose | ☐ |
| CT Call Method | POINT_OF_ACCELERATION ▽ |
| CT Call Threshold | 0.3 |

| PCR Baseline Detection Parameters | |
|---|---|
| Baseline Slope Tolerance | 0.03 |
| Maximum Refinement Steps | 1 |
| Number of Smoothing Points | 11 |
| Minimum Length | 5 |
| Minimum Start Index | 0 |
| Allowable Dog Leg | 0.3 |
| Maximum Hole Length | 0.3 |

| TM Data Reduction Parameters | |
|---|---|
| Smooth Mode | GORRY ▽ |
| Smooth Width | 3 |
| Smooth Order | 3 |
| Median Filter Width | 3 |
| Noise Cutoff Mode | CUTOFF_VFS ▽ |
| Median Filter Width | 0.075 |
| Peak Cutoff Mode | CUTOFF_VFS ▽ |
| Peak Positive Cutoff Factor | 0.2 |
| Peak Negative Cutoff Factor | 0.2 |
| Spline Sample Rate | 25 |
| Spline Search Radius | 0.5 |
| Take Derivative | ☑ |
| Is Quenching | ☑ |
| Median Polish Bandwidth | 11 |
| Median Polish Iterations | 4 |
| Enhancement Mode | ENHANCE_NONE ▽ |
| Enhancement Blend Factor | 0.1 |
| Enhancement Fold Increase | 2 |

500

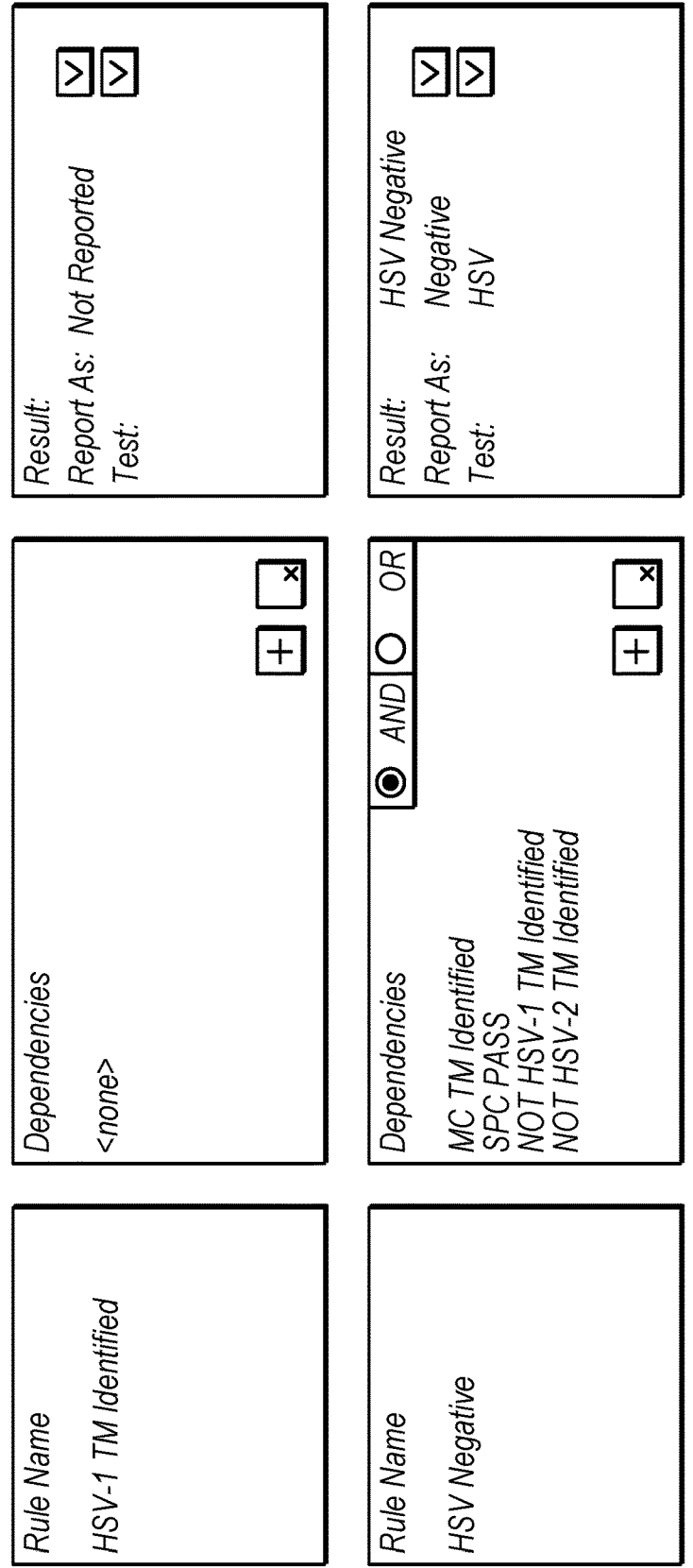

REPORTING RULES

| Result Logic | | | Return |
|---|---|---|---|
| IF | HSV Positive ˅ | THEN | Detected |
| ELSE IF | HSV Negative ˅ | THEN | Not Detected |
| ELSE IF | MC Fail ˅ | THEN | N/A |
| ELSE IF | Invalid no CT ˅ | THEN | Invalid |
| ELSE | | | Not Detected |

FIG. 8A ⤴ 800

GRAPHING RULES

| Channel | Rule Type | Condition | Restrict Range | Range Low | Range High | X-Axis Offset |
|---|---|---|---|---|---|---|
| 2 | Melt | HSV Positive ˅ | No ˅ | 0 | 0 | deltaTemp |
| 2 | PCR | HSV Negative ˅ | No ˅ | 0 | 0 | <none> |

| Line | SPC CT | SPC TM | HSV CT | HSV-2 TM | HSV-1 TM | MC TM | Result | Type | Ch2 | Ch4 | Ch6 | Ch2 CT | Ch2 TM | Ch4 CT | Ch4 TM | Ch 6 TM |
|---|---|---|---|---|---|---|---|---|---|---|---|---|---|---|---|---|
| 1 | + | + | + | + | + | + | HSV-1&2 Positive | Positive | Detected | N/A | Pass | 0 | 0.00,0.00 | | | 0 |
| 2 | - | + | + | + | + | + | HSV-1&2 Positive | Positive | Detected | N/A | Pass | 0 | 0.00,0.00 | | | 0 |
| 3 | + | - | + | + | + | + | HSV-1&2 Positive | Positive | Detected | N/A | Pass | 0 | 0.00,0.00 | | | 0 |
| 4 | - | - | + | + | + | + | HSV-1&2 Positive | Positive | Detected | N/A | Pass | 0 | 0.00,0.00 | | | 0 |
| 5 | + | + | - | + | + | + | HSV Invalid | Invalid | Invalid | N/A | Pass | Invalid | Invalid | | | 0 |
| 6 | - | + | - | + | + | + | HSV Invalid | Invalid | Invalid | N/A | Pass | Invalid | Invalid | | | 0 |
| 7 | + | - | - | + | + | + | HSV Invalid | Invalid | Invalid | N/A | Pass | Invalid | Invalid | | | 0 |
| 8 | - | - | - | + | + | + | HSV Invalid | Invalid | Invalid | N/A | Pass | Invalid | Invalid | | | 0 |
| 9 | + | + | + | - | + | + | HSV-1 Positive | Positive | Detected | N/A | Pass | 0 | 0.00,0.00 | | | 0 |
| 10 | - | + | + | - | + | + | HSV-1 Positive | Positive | Detected | N/A | Pass | 0 | 0.00,0.00 | | | 0 |
| 11 | + | - | + | - | + | + | HSV-1 Positive | Positive | Detected | N/A | Pass | 0 | 0.00,0.00 | | | 0 |
| 12 | - | - | + | - | + | + | HSV-1 Positive | Positive | Detected | N/A | Pass | 0 | 0.00,0.00 | | | 0 |
| 13 | + | + | - | - | + | + | HSV Invalid | Invalid | Invalid | N/A | Pass | Invalid | Invalid | | | 0 |
| 14 | - | + | - | - | + | + | HSV Invalid | Invalid | Invalid | N/A | Pass | Invalid | Invalid | | | 0 |
| 15 | + | - | - | - | + | + | HSV Invalid | Invalid | Invalid | N/A | Pass | Invalid | Invalid | | | 0 |
| 16 | - | - | - | - | + | + | HSV Invalid | Invalid | Invalid | N/A | Pass | Invalid | Invalid | | | 0 |
| 17 | + | + | + | + | - | + | HSV-2 Positive | Positive | Detected | N/A | Pass | 0 | 0.00,0.00 | | | 0 |
| 18 | - | + | + | + | - | + | HSV-2 Positive | Positive | Detected | N/A | Pass | 0 | 0.00,0.00 | | | 0 |
| 19 | + | - | + | + | - | + | HSV-2 Positive | Positive | Detected | N/A | Pass | 0 | 0.00,0.00 | | | 0 |
| 20 | - | - | + | + | - | + | HSV-2 Positive | Positive | Detected | N/A | Pass | 0 | 0.00,0.00 | | | 0 |
| 21 | + | + | - | + | - | + | HSV Invalid | Invalid | Invalid | N/A | Pass | Invalid | Invalid | | | 0 |
| 22 | - | + | - | + | - | + | HSV Invalid | Invalid | Invalid | N/A | Pass | Invalid | Invalid | | | 0 |
| 23 | + | - | - | + | - | + | HSV Invalid | Invalid | Invalid | N/A | Pass | Invalid | Invalid | | | 0 |
| 24 | - | - | - | + | - | + | HSV Invalid | Invalid | Invalid | N/A | Pass | Invalid | Invalid | | | 0 |
| 25 | + | + | - | - | - | + | HSV Negative | Negative | Not Detec | Pass | Pass | ND | | | 0 | 0 |
| 26 | - | + | - | - | - | + | HSV Invalid | Invalid | Not Detec | Fail | Pass | ND | | Fail | Fail | 0 |
| 27 | + | - | - | - | - | + | HSV Invalid | Invalid | Not Detec | Fail | Pass | ND | | Fail | Fail | 0 |
| 28 | - | - | - | - | - | + | HSV Invalid | Invalid | Not Detec | Fail | Pass | ND | | Fail | Fail | 0 |
| 29 | + | + | - | - | - | - | HSV Negative | Negative | Not Detec | Pass | Pass | ND | | | 0 | 0 |
| 30 | - | + | - | - | - | - | HSV Invalid | Invalid | Not Detec | Fail | Pass | ND | | Fail | Fail | 0 |
| 31 | + | - | - | - | - | - | HSV Invalid | Invalid | Not Detec | Fail | Pass | ND | | Fail | Fail | 0 |
| 32 | - | - | - | - | - | - | HSV Invalid | Invalid | Not Detec | Fail | Pass | ND | | Fail | Fail | 0 |
| 33 | + | + | + | + | + | - | HSV Invalid | Invalid | N/A | N/A | Fail | N/A | N/A | N/A | N/A | Fail |

DETAILED ASSAY PROTOCOL SPECIFICATION

This application claims the benefit of U.S. Provisional Application No. 62/092,121, filed on Dec. 15, 2014, which is incorporated by reference herein in its entirety.

BACKGROUND

Technical Field

This disclosure relates to assay devices and more particularly to techniques for detailed assay configuration.

Description of the Related Art

Assay devices are often used to determine characteristics of test samples, e.g., using polymerase chain reaction (PCR), Deoxyribonucleic Acid (DNA) melt techniques, or immunoassay techniques. Typically, an assay device has software/ circuitry configured to perform instrument control (e.g., run motors, optics, heaters, etc.) and run the assay protocol. This, however, can make it difficult to develop new or modified assays because changes to the assay protocol may require extensive re-validation of the assay device software or at least the reconfigured portions. This can increase costs and delay the time to market of new or modified diagnostic assays that require regulatory clearance or approval. In addition, assay device users and third party developers may have no ability or only limited ability to create new or customized assay protocols and generate customized reports based on user-specified information if changes to the assay device software are required.

SUMMARY

Various embodiments of the present invention provide solutions to the problems identified above by, for example, providing a system in which assay device software is separated from assay configuration software. As such, each assay protocol may be designed for a specific test and specify, for example, sample preparation steps, thermal steps, signal processing, call logic evaluation, and reporting functionality. The assay protocol file can be created and saved on the assay device or imported and saved on the assay device. The assay device may be agnostic to the assay configuration software. Accordingly, new assay protocols or changes to existing assay protocols are easier to make and do not require extensive re-validation of the software and/or hardware of the assay device. This may facilitate the development of new or modified assays by the manufacturer as well as by the end user or a third party assay developer. This should reduce time to market for assays and increase the utility of assay device to end users.

According to one embodiment, a non-transitory computer-readable medium has instructions stored thereon that are executable by a computing device to perform the following operations. In this embodiment, the operations include presenting a user configuration tool for an assaying device. In this embodiment, the operations include generating first configuration information and second configuration information. In this embodiment, the first configuration information specifies a sequence of operations for an assay to be performed by the assaying device and specifies a set of parameters for the sequence of operations. In this embodiment, the second configuration information specifies a set of rules for selection of an outcome from among a plurality of potential outcomes of the assay, and the user input specifies at least one new rule for the set of rules. In this embodiment, the first configuration information is usable by the assaying device to perform the sequence of operations based on the set of parameters to generate data for a sample. The data may be, for example, fluorescence data (e.g., wavelength, intensity, etc.), electrochemical data (e.g., current, voltage, etc.), chemiluminescence data, bioluminescence data, or mass spectrometry data. In this embodiment, the second configuration information is usable to process the data based on the set of rules to generate an outcome for the assay.

According to a second embodiment, a computer-implemented method includes causing a user configuration tool for an assaying device to be displayed. In this embodiment, the method further includes generating first and second configuration information. In this embodiment, the first configuration information specifies a sequence of operations for an assay to be performed by the assaying device and specifies a set of parameters for the sequence of operations. In this embodiment, the second configuration information specifies a set of rules for selection of an outcome from among a plurality of potential outcomes of the assay, and the user input specifies at least one new rule for the set of rules. In this embodiment, the first configuration information is usable by the assaying device to perform the sequence of operations based on the set of parameters to generate data for a sample the second configuration information is usable to process the data based on the set of rules to generate an outcome for the assay. The data may be, for example, fluorescence data (e.g., wavelength, intensity, etc.), electrochemical data (e.g., current, voltage, etc.), chemiluminescence data, bioluminescence data, or mass spectrometry data.

In one embodiment, the method includes loading the assaying device with a sample that includes nucleic acids. In this embodiment, the assaying device performs the sequence of operations based on the set of parameters to generate amplified nucleic acids in the sample. In this embodiment, the method may include processing, based on the set of rules, data (e.g., fluorescence data) generated by the sequence of operations to generate an outcome for the assay. The sample may be loaded before or after transfer of the second configuration information to the assaying device.

According to a third embodiment, a system includes one or more processors and one or more memories. In this embodiment, the one or more memories have instructions stored thereon that are executable by the one or more processors to cause the apparatus to perform the following operations. In this embodiment, the operations include presenting a user configuration tool for an assaying device. In this embodiment, the operations include generating first and second configuration information. In this embodiment, the first configuration information specifies a sequence of operations for an assay to be performed by the assaying device and specifies a set of parameters for the sequence of operations. In this embodiment, the second configuration information specifies a set of rules for selection of an outcome from among a plurality of potential outcomes of the assay, wherein the user input specifies at least one new rule for the set of rules. In this embodiment, the first configuration information is usable by the assaying device to perform the sequence of operations based on the set of parameters to generate data for a sample the second configuration information is usable to process the data based on the set of rules to generate an outcome for the assay. The data may be, for example, fluorescence data (e.g., wavelength, intensity, etc.), electrochemical data (e.g., current, voltage, etc.), chemiluminescence data, bioluminescence data, or mass spectrometry data.

According to a fourth embodiment, a system includes a first computing device and a second computing device, where the second computing device is distinct from the first computing device and is included in an assaying device. In this embodiment, the first computing device is configured to present a user configuration tool for the assaying device. In this embodiment, the first computing device is configured to generate, based on user input, first configuration information that specifies a sequence of operations for an assay to be performed by the assaying device and specifies a set of parameters for the sequence of operations. In this embodiment, the first computing device is configured to generate, based on user input, second configuration information that specifies a set of rules for selection of an outcome from among a plurality of potential outcomes of the assay. In this embodiment, the user input specifies at least one new rule for the set of rules. In this embodiment, the second computing device is configured to receive the first and second configuration information, cause the assay device to perform the sequence of operations based on the set of parameters to generate data for a sample, and process the data based on the set of rules to generate an outcome for the assay. The data may be, for example, fluorescence data (e.g., wavelength, intensity, etc.), electrochemical data (e.g., current, voltage, etc.), chemiluminescence data, bioluminescence data, or mass spectrometry data.

BRIEF DESCRIPTION OF THE DRAWINGS

FIG. 3 shows one embodiment of a user interface usable to input assay settings.

FIG. 4 shows one embodiment of a user interface usable to input thermal parameters.

FIG. 5 shows one embodiment of a user interface usable to input analysis parameters.

FIG. 7 shows one embodiment of a user interface usable to add and/or configure call logic rules FIG. 8A shows one embodiment of a user interface usable to input reporting rules.

FIG. 8B shows one embodiment of a user interface usable to input graphing rules.

FIG. 9 shows one embodiment of a truth table generated based on call logic rules.

TERMS

The following paragraphs provide definitions and/or context for terms found in this disclosure (including the appended claims).

"Embodiment." This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

"Based On." As used herein, this term is used to describe one or more factors that affect a determination. This term does not foreclose additional factors that may affect a determination. That is, a determination may be solely based on those factors or based only in part on those factors. Consider the phrase "determine A based on B." This phrase connotes that B is a factor that affects the determination of A, but does not foreclose the determination of A from also being based on C. In other instances, A may be determined based solely on B.

"Configured To" or "Operable To." Various units, circuits, or other components may be described or claimed as "configured to" perform a task or tasks. In such contexts, the phrases "configured to" and "operable to" may be used to connote structure by indicating that the units/circuits/components include structure (e.g., circuitry) that performs the task or tasks during operation. As such, the unit/circuit/component can be said to be configured to perform the task even when the specified unit/circuit/component is not currently operational (e.g., is not on). The units/circuits/components used with the "configured to" language include hardware—for example, circuits, memory storing program instructions executable to implement the operation, etc. Reciting that a unit/circuit/component is "configured to" perform one or more tasks is expressly intended not to invoke 35 U.S.C. § 112(f) for that unit/circuit/component.

It is to be understood the present disclosure is not limited to particular devices or methods, which may, of course, vary. It is also to be understood that the terminology used herein is for the purpose of describing particular embodiments only, and is not intended to be limiting. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

DETAILED DESCRIPTION

Figure 1:
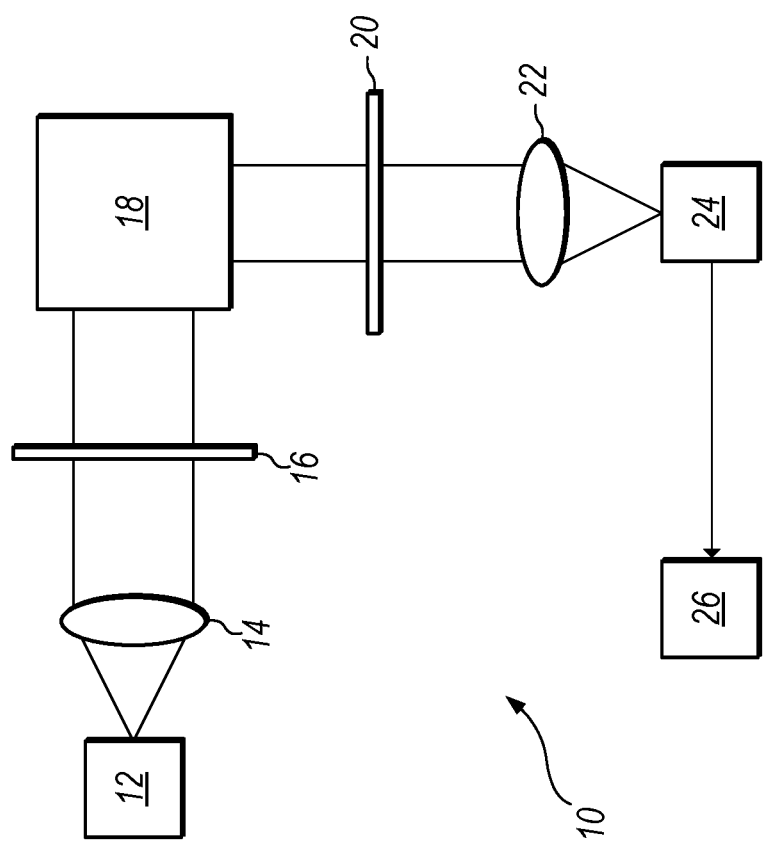
FIG. 1 shows a schematic of an embodiment of a PCR device.
Figure 2:
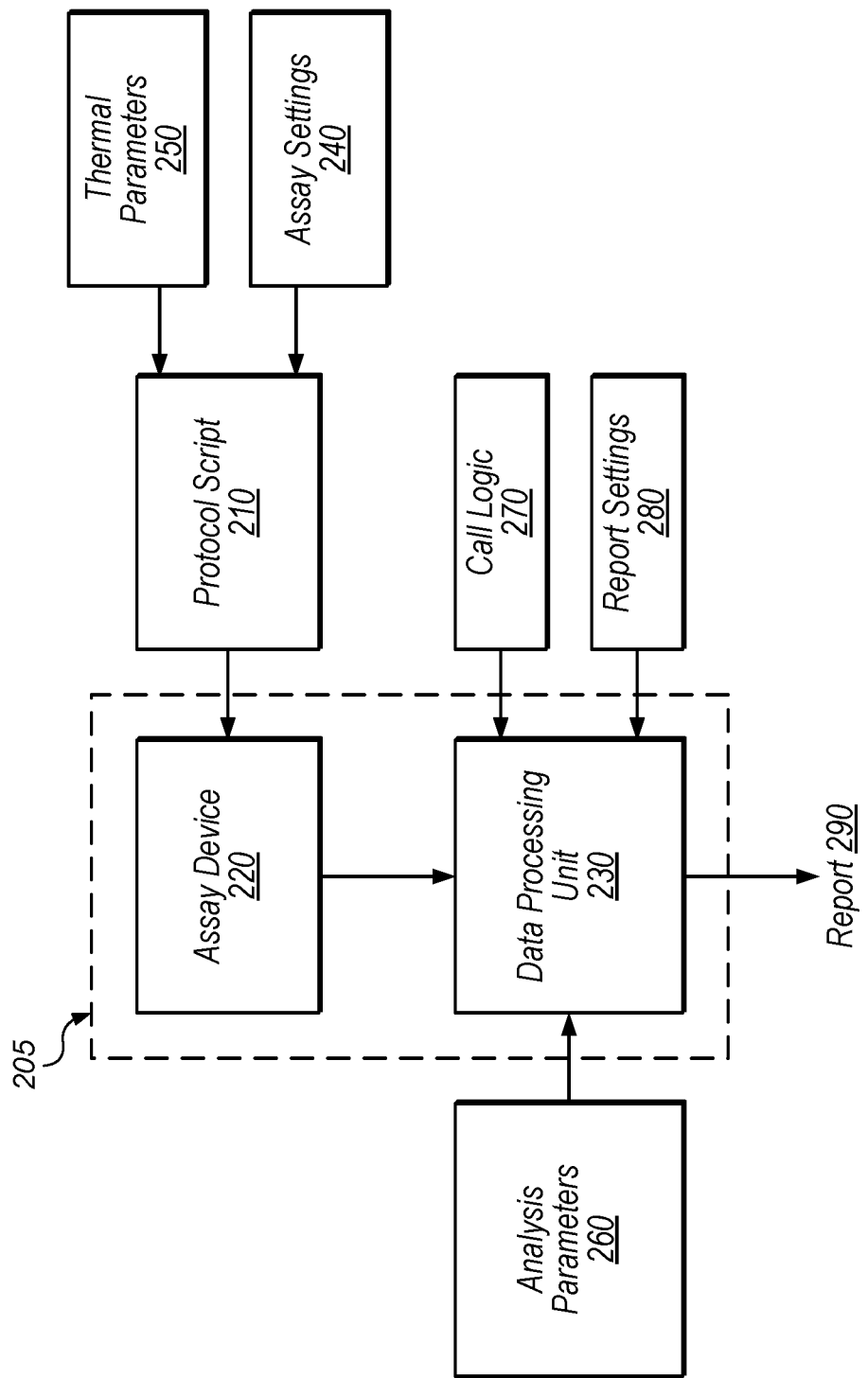
FIG. 2 shows a block diagram illustrating information flow for an assay according to one embodiment.

This disclosure initially describes, with reference to FIG. 1, an exemplary PCR system. FIG. 2 shows information flow for specification of assay procedures and/or analysis according to one embodiment. Exemplary user interfaces for specification of various parameters are described with reference to FIGS. 3-9. An assay report output is described with reference to FIG. 10 while a method for assay parameter specification is described with reference to FIG. 11. An exemplary computing device is described with reference to FIG. 12.

This disclosure includes techniques of general applicability that may be applied in different situations according to various embodiments. For example, this disclosure includes techniques that may be applicable in single-tube polymerase chain reaction (PCR) or DNA melt analysis, PCR or melt data from neighboring wells of a multi-well plate or other multi-well arrangement, capillary electrophoresis data (e.g., DNA sequencing), gas chromatography, multispectral imaging, dual-color fluorescence correlation spectrometry, immunoassays, etc.

Overview of Exemplary PCR Embodiments

Turning now to FIG. 1, a block diagram illustrating one embodiment of a polymerase chain reaction (PCR) imaging system 10 according to the present disclosure is shown. This disclosure is of course not limited to PCR devices, but FIG. 1 is provided to give context for one exemplary embodiment. In the illustrated embodiment, this system includes light source 12, input lens 14, input filter 16, PCR tube 18 (which may be a consumable element configured to hold a sample and to be inserted into a heat block of the PCR device), output filter 20, output lens 22, detector 24, and analysis hardware 26.

Many embodiments of PCR devices are well-known in the art, and this disclosure may find applicability in any suitable system. For example, this disclosure may be used in conjunction with real-time PCR systems, single-tube PCR systems, multi-well PCR systems, quantitative PCR systems, other assaying systems and devices, etc.

It is to be noted that some aspects of this disclosure refer to PCR embodiments in which the fluorescence signal decreases with time (or with cycle number). This is due to the use of a quenching reaction in some embodiments. One of ordinary skill in the art will recognize the modifications that may be made in the case of a PCR reaction in which fluorescence increases with time instead of decreasing.

In PCR imaging system 10, light source 12 provides illumination to excite various fluorescent species (e.g., fluorophores) within PCR tube 18. In various locations throughout this disclosure, the fluorophore FAM may be referred to; however, many fluorescent species are known in the art, and these two are provided only for illustrative purposes.

The illumination from light source 12 may be focused or collimated by input lens 14 and wavelength-filtered by input filter 16. In some embodiments, light source 12 may be a broad-spectrum source (e.g., white light), with wavelength selectivity provided by input filter 16. In other embodiments, however, light source 12 may itself be narrow-spectrum (e.g., an LED or laser light source). In these embodiments, it may be possible to omit input filter 16.

During the course of the reaction carried out in PCR tube 18, fluorescent light emitted by the various fluorescent species within PCR tube 18 may be captured by detector 24. In some embodiments, the fluorescent light may first be wavelength-filtered at output filter 20 and/or focused at output lens 22 before being detected at detector 24. Detector 24 may be any suitable light detector, such as a photodetector, charge-coupled device (CCD) detector, photomultiplier tube, etc. Analysis hardware 26 then receives data from detector 24. Analysis hardware 26 may include any suitable computing device as known in the art, and may include one or more processors, memory, and/or non-transitory computer-readable media. The elements of PCR imaging system 10 may be integrated into a single device, or they may be connected together from separate elements. Analysis hardware 26 may be used to carry out any of the methods disclosed herein.

Exemplary Assay Protocol Specification

The techniques described herein may allow a user to create or modify an assay. In an exemplary embodiment discussed below with reference to FIGS. 3-10, an example assay for detecting herpes simplex virus (HSV) is described, but similar techniques may be used for any of various assay types. In the HSV example, results of the assay may indicate whether a patient has HSV, based on a detected cycle threshold for a PCR phase and a detected melt temperature for a melt phase of the assay.

In the HSV example, an assay typically includes the following steps: sample preparation, cycling (e.g., PCR thermal cycling or melt thermal cycling), signal processing, call logic evaluation, and reporting. A user may insert a sample that includes nucleic acids into an assay device, and performance of the assay may generate amplified nucleic acids in the sample for analysis and reporting.

Referring now to FIG. 2, a block diagram of information flow according to one embodiment is shown. In the illustrated embodiment, assay device 220 is configured to perform one or more assays on one or more samples and provide results to data processing unit 230. In some embodiments, assay device 220 and/or data processing unit 230 correspond to the PCR imaging system 10, discussed above with reference to FIG. 1.

Figure 10:
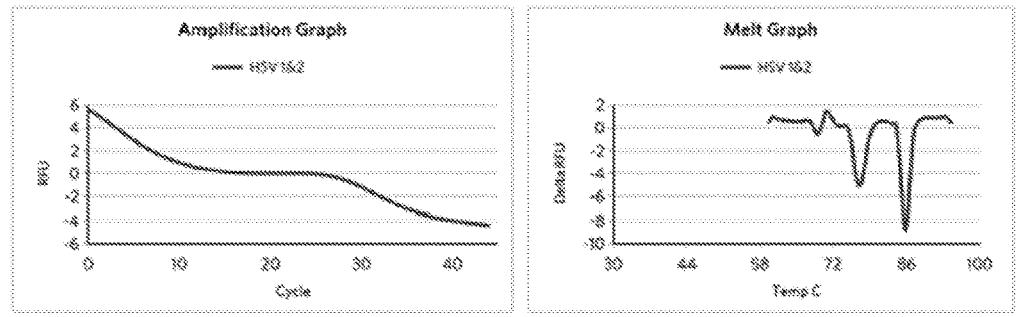
FIG. 10 shows one embodiment of an assay report.

In the illustrated embodiment, data processing unit 230 is configured to generate a report 290 based on the results (an exemplary HSV report is shown in FIG. 10). In the illustrated embodiment, one or more of protocol script 210, assay settings 240, thermal parameters 250, analysis parameters 260, call logic 270, and report settings 280 may be added and/or modified by a user.

Figure 6A:
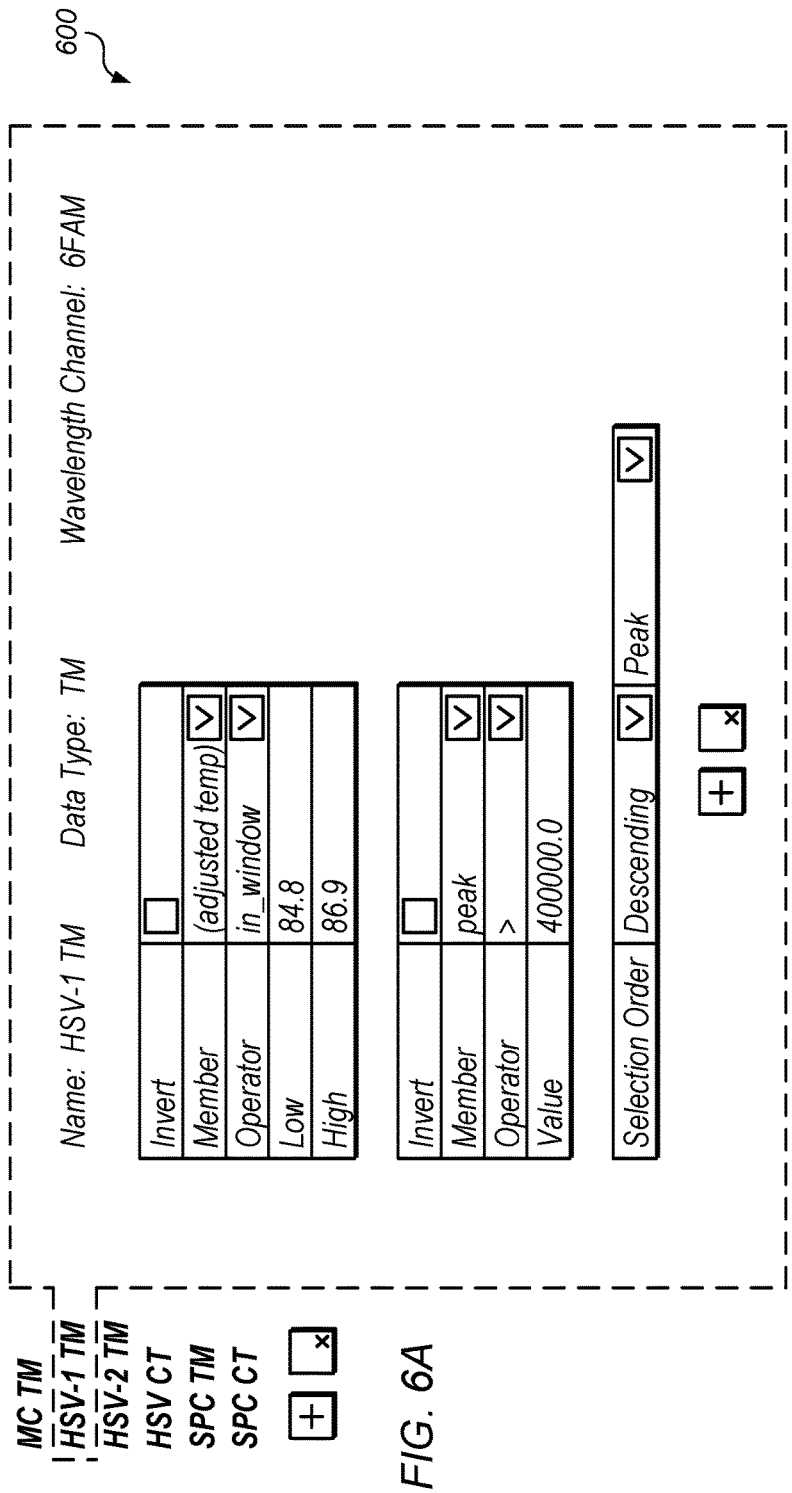
FIG. 6A shows one embodiment of a user interface usable to specify parameters for detecting TM, CT, and/or RFU conditions.
Figure 6B:
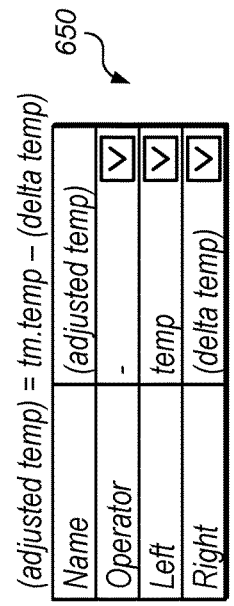
FIG. 6B shows one embodiment of a user interface usable to specify user-defined variables.

With reference to the HSV example, a user may create and/or modify: assay settings 240 such as dyes and channels used for HSV as shown in FIG. 3, thermal parameters 250 such as denature or anneal temperatures as shown in FIG. 4, protocol script 210 as discussed in further detail below, analysis parameters 260 such as signal processing parameters as shown in FIG. 5, parameters for detecting/naming assay characteristics (such as detecting a melting temperature in a particular window above a specified peak value, for example) as shown in FIGS. 6A-6B, call logic rules 270 for determining assay results (such as whether a patient has HSV) as shown in FIG. 7, and/or reporting rules for configuring what information is reported as shown in FIGS. 8A-8B.

For example, a user may modify a pre-existing HSV assay by designing a new call logic rule (and/or a dependency between call logic rules) to improve assay detection accuracy. As another example, a user may specify additional call logic rules such as sample type or demographic information. Said another way, users may specify what (if any) additional information is needed to make a call for a given assay, while allowing the assay device to remain agnostic to the details of the assay file. The disclosed techniques may also allow development of assays by parties who do not provide assay devices. For example, consider an HSV assay that included only a PCR step and did not include a melt step. For this assay, the user could add a melt step, and specify that an HSV positive result is returned only if both an expected cycle count for the PCR step and an expected melting temperature are detected (a logical "and" dependency).

The disclosed techniques may reduce validation requirements when configuring assay protocols. For example, in some embodiments, parameters are specified on a separate computing device rather than the assay device and/or data processing unit, allowing separation between assay configuration software and assay device software/hardware. Thus, changing the assay parameters may not require a re-validation of the assay device or assay device software.

In embodiments in which user-specified information for an assay is generated using a computing system that is distinct from assay device 220, a computer program configured to generate this information may be disjoint from any programs running on assay device 220 and/or data processing unit 230. In this embodiment, the protocol script 210, assay settings 240, thermal parameters 250, analysis parameters 260, call logic 270, and/or report settings 280 may be generated by the distinct computing system and downloaded to assay device 220 (which may or may not include data processing unit 230).

In this embodiment, assay device 220 may include software and/or circuitry configured to (1) perform instrument-specific calibration routines, (2) perform pre-processing based on the calibration routines (e.g., to normalize raw data), and (3) perform instrument control. The software/circuitry configured to perform instrument control may provide an interface between user-specified assay information (which may be generated based on user interaction with the distinct computing system, as discussed above, rather than by assay device 220) and other parts of assay device 220 that are configured to run motors, optics, heaters, etc. Thus, assay device 220 may perform one or more assays and generate one or more reports based on the user-specified information. In this embodiment, changes to the various user-specified information may not require re-validation of the software and/or hardware of assay device 220. This may allow third parties to develop new or modified assays and/or facilitate development of new assays by a vendor of assay device 220. This may reduce time to market for assays and increase the utility of assay device 220 to end users.

Exemplary embodiments of interfaces for configuring the various different parameters are described below with reference to FIGS. 3-8. However, the various combinations of parameters described herein are illustrative only. In other embodiments, additional parameters may be specified and/or disclosed parameters may be omitted. The various interfaces shown in FIGS. 3-8 may be graphical user interfaces (GUIs), for example, and may be displayed by a computing system that is separate from assay device 220.

Exemplary Assay Settings

Turning now to FIG. 3, one embodiment of a user interface 300 usable to input assay settings is shown. In the illustrated embodiment, an assay name, assay type, and whether or not the assay is a starter assay is specified. In this particular example, the assay is for HSV and is an in vitro diagnostic (IVD) assay. In the illustrated example, a description field has not been filled in.

In the illustrated embodiment, dyes have been assigned for channels 2, 4, and 6, while channels 1, 3, and 5 are unused. In the illustrated embodiment, FAM is used as a fluorophore for HSV while AP559 and AP662 dyes are used for sample processing control (SPC) and melt calibration (MC). In this HSV example, the SPC is used to ensure that a reaction actually occurred, and a sample may be retested if SPC is not detected to avoid a false negative. The melt calibration may be used to control for instrument variation and allow calibration of detected melting temperatures.

Exemplary Protocol Script and Parameters

Protocol script 210 may specify what operations occur in what ordering for a given assay. The following exemplary pseudocode for one embodiment of a protocol script 210 specifies preparation, PCR, and melt phases of the exemplary HSV assay:

1. if (!MotorsHomed) then Home All Motors
2. if (SamplePrepEnabled) then {
3. Start Sample Prep
4. if (!RtPcrEnabled & !MeltEnabled) then No Oil Dispense
5. else Execute Oil Dispense Sequence
6. }
7. if (RtPcrEnabled) then {
8. StartRtPcr
9. if (NumPcrSteps==2) then Execute 2-step RT-PCR Sequence
10. else Execute 3-step RT-PCR Sequence
11. else RT-PCR Not Executed
12. }
13. if (MeltEnabled) then {
14. Execute Melt Sequence
15. Turn Heater On
16. Lock Cassette for PCR
17. Start Melt
18. End Melt
19. }

In this example, at line 1, if motors have not been homed, they are moved to a home position. At line 2, if sample preparation is enabled, then sample prep is started and oil may be dispensed. At line 7, a determination is made as to whether a PCR step is enabled, and the PCR step is performed based on lines 8-11 if so. At line 13, a determination is made as to whether a melt step is enabled, and the melt step is performed based on lines 14-18 if so. Thus, in the illustrated embodiments, phases of the assay may be enabled or disabled using the SamplePrepEnabled, RtPcrEnabled, and MeltEnabled parameters. In various embodiments, any of various assay portions may be similarly enabled or disabled. In some embodiments, a user interface allows a user to add functions to a protocol script or modify operations specified by the protocol script.

Further, various parameters for operations in the protocol script may be specified by a user. For example, operations such as "Start Sample Prep," "Execute 2-step RT-PCR Sequence," "Start Melt" etc. may be function calls that may be passed various parameters. Exemplary thermal parameters that may be passed to these functions are described below with reference to FIG. 4. In one embodiment, the assay settings 240 of FIG. 3 (e.g., channel selection, tests, and dyes) are also used as input to the protocol script, e.g., using input variables. The exemplary pseudocode provided above is illustrative only and is not intended to limit the scope of the present disclosure.

Turning now to FIG. 4, one embodiment of a user interface 400 usable to specify thermal parameters 250 is shown. In the illustrated embodiment, thermal parameters are separately specified desired temperatures and timing during a pre-PCR phase, a PCR phase, and a melt phase of an assay. In the illustrated embodiment, check boxes may be used to enable or disable each of these phases. In the illustrated embodiment, rectangles with downwards pointing arrows (e.g., next to the "2" for the for "Number of PCR Steps" field) indicate a drop-down menu, while other fields allow free-form entry. In various embodiments, any of various appropriate interfaces may be implemented to specify appropriate values, operands, etc.

In the illustrated embodiment, various temperature, hold time, activation time, number of steps, optical read location, number of cycles, denature time, start/final temperature, and step sizes are shown. In various embodiments, any appropriate combinations of these parameters and/or additional parameters may be specified.

Specification of thermal parameters 250 separately from protocol script 210 may allow the same protocol script to be used for multiple different assays that have different thermal parameters. In other embodiments, thermal parameters may be specified explicitly within protocol script 210 rather than being specified separately.

The protocol script, assay settings, and thermal parameters described above may generally be described as assay configuration information that specifies performance of an assay itself. The parameters and rules described below with reference to FIGS. 5-8 generally relate to analysis and reporting information used to configure processing of raw outputs from the assay and reporting results of the assay.

Exemplary Analysis Parameters and Call Logic Rules

Turning now to FIG. 5, one embodiment of a user interface 500 usable to input analysis parameters 260 is shown. The analysis parameters may be used to configure signal processing of raw assay data. In the illustrated example, the "wavelength channel" dropdown menu allows selection of the channel for which the parameters are being specified. In the illustrated embodiment, various signal processing and detection parameters are shown.

For example, the illustrated PCR data reduction parameters include: slope norm target, number of smoothing points, quenching, verbose, cycle threshold (CT) call method, and CT call threshold. The illustrated PCR baseline detection parameters include: baseline slope tolerance, maximum refinement steps, number of smoothing points, minimum length, minimum start length, allowable dog leg, and maximum hole length. The illustrated melting temperature (TM) reduction parameters include: smooth mode, smooth width, smooth order, median filter widths, noise cutoff mode, peak cutoff mode, cutoff factors, spline sample rate and search radius, derivative, quenching, median polish bandwidth and iterations, enhancement mode, blend factor, and fold increase. In various embodiments, any appropriate combinations of these parameters and/or additional parameters may be specified.

In one embodiment, based on analysis parameters 260, data processing unit 230 is configured to generate a set of data structures for the assay. In one embodiment, this set may include melt temperature (TM) structures which may be used for melt analysis, cycle threshold (CT) structures which may be used for PCR analysis, and/or relative fluorescent unit (RFU) structures. These structures may be used as input to call logic rules, which may determine an assay result based on values stored in fields of the relevant data structures.

Each structure may have one or more fields. For example, a TM structure may have at least "temp" and "peak" fields, while a CT structure may include at least "cycle" and "rfu" fields. An RFU structure may have mean, min, standard deviation, and max fields, for example. These fields may be filled based on processed assay outputs. Further exemplary TM fields according to some embodiments include: max/min signal values, spline refined peak locations, peak locations based on one or more derivatives of the signal, distances from peak to baseline, area under curve, peak symmetry, slope, widths of the peak, Gaussian fits to the peak, etc. Further exemplary CT fields according to some embodiments include: confidence, baseline information, etc.

FIG. 6A shows one embodiment of a user interface 600 usable to detect and name a particular TM, CT, or RFU structure based on specified rules or parameters. In some embodiments, the parameters of FIGS. 6A-6B are included in analysis parameters 260. In the illustrated example, the name "HSV-1 TM" has been selected. Other currently-defined names for this exemplary assay include MC TM, HSV-2 TM, HSV CT, SPC TM, and SPC CT. The icons below the available names allow a user to add or delete names for the assay, in the illustrated embodiment.

In the embodiment of FIG. 6A, the illustrated parameters indicate that HSV-1 will be identified as the 1st TM structure from channel 6FAM when ordered by descending peak satisfying the condition that "adjusted temp" of the TM structure is in the window between 84.8 and 86.9 AND has a peak greater than 400000.0. The icons near the bottom of FIG. 6A allow a user to add or remove parameters used to identify a particular TM, CT, or RFU structure.

In the illustrated embodiment, the in_window and > (greater than) operators are shown. In some embodiments, various operators may be selected, including arithmetic operators such as + (addition), − (subtraction), = (comparison), / (division), * (multiplication), < (less than), CT found, and midpoint operators may be used. The result of various operations may be a floating point value or a true/false value, depending on the operator and expression.

FIG. 6B shows one embodiment of a user interface 650 usable to specify a user-defined field, which may be used in identifying a TM, CT, or RFU structure, for example. In the illustrated embodiment, "delta temp" is determined based on MC TM. For example, in one embodiment, the expected melting temperature for the melt calibrator is 72.0 degrees. In this embodiment, delta temp is specified (e.g., using an interface similar to FIG. 6B) as the actual MC TM "temp" minus 72.0 degrees. An interface similar to that of FIG. 6B may be used to specify delta temp. In the illustrated embodiment, the adjusted temp for HSV-1 TM is determined as the "temp" field value of a given structure minus "delta temp." This allows a user to perform various arithmetic and/or logical operations on various fields and use the results as inputs to structure identification parameters and/or call logic rules. When selecting values for operations (e.g., temp, delta temp, etc.), a member of a current structure (which may be referred to as a "this" operand) may be selected, a literal value may be provided (e.g., a floating-point number), or a member of another structure (which may be referred to as a "selection" operand) may be specified. In some embodiments (not shown), a user interface allows a user to select one of these three options for a value and provides suitable options based on the selection (e.g., a text entry field for a floating-point value or a list of available member fields of the current structure).

Turning now to FIG. 7, one embodiment of a user interface 700 usable to add and/or modify call logic rules 270 is shown. In the illustrated embodiment, two rules are shown: an "HSV-1 TM Identified" rule and an "HSV Negative" rule. In the illustrated embodiment, each rule includes fields for Rule Name, Dependencies, and Result. In the illustrated embodiment, the icons near the bottom of interface 700 may be used to add or remove rules.

The HSV-1 TM Identified rule, in the illustrated example, does not have any dependencies and is not reported. In this embodiment, HSV-1 TM Identified may evaluate as true in response to identification of a TM structure that meets the requirements specified in FIG. 6A. Thus, if such a structure cannot be identified (indicating that the expected melt temperature was not found), this rule evaluates as false. In the illustrated embodiment, the graphics in the lower-right corner of the dependencies field may be used to add and delete logical dependencies between rules.

The HSV Negative rule, in the illustrated embodiment, is dependent on the HSV-1 TM Identified rule as well as several other rules (SPC PASS, NOT HSV-1 TM Identified, and NOT HSV-2 TM Identified). In the illustrated example, the "AND" graphic has been selected (rather than the "OR" graphic) to use this logical relationship between the rules on which HSV Negative depends. Thus, in this example, HSV Negative is evaluated only if all of the rules on which it depends are true. The ability to specify logical relationships and hierarchies of rules allows flexible specification of any desired logical combination, while the techniques described with reference to FIGS. 6A-6B allow specification of various thresholds, operators, windows, etc. for each rule.

In some embodiments, a call logic dependency can be based on another rule or the logical negation of another rule. In some embodiments, user interface 700 is configured to prevent a user from creating a dependency cycle. For example, if rule 1 depends on rule 2 and rule 2 depends on rule 3, the interface may prevent the user from creating a dependency for rule 3 on rule 1, because this would create a cycle.

As another example of a rule (not shown), for a flu assay, a "Flu A High CT" rule may evaluate as TRUE when there is a CT structure defined for Flu A CT as named and has a "cycle" value greater than 38.0.

In the illustrated embodiment, user interface 700 allows a user to enter a new rule (rather than simply modifying a previously existing rule) and define dependencies between the new rule and one or more other rules. Thus, in various embodiments, users may add and/or modify call logic rules to configure the conditions under which various assay results will be indicated.

In the illustrated embodiment, HSV Negative is reported only if an MC TM has been identified, allowing calibration for detection of the HSV TMs. Similarly, HSV Negative is reported only if SPC PASS is true. The SPC may be used to ensure that a reaction actually happened, to avoid calling a false negative. If the SPC is not passed, HSV Negative is not reported. Instead, in one embodiment, the assay is reported as invalid, indicating that the sample should be retested.

In other embodiments, users may specify any of various additional appropriate rules. For example, a user may specify a patient demographic, a sample type, etc. that is needed to make a call. The call may not be made unless the user-specifies information is present and/or within a specified range, category, etc. Users may specify such rules, along with any desired dependencies on other rules, via embodiments of the user interface 700.

Turning now to FIG. 8A, one embodiment of a user interface 800 usable to input reporting rules is shown. Reporting rules may be used in various embodiments to control how information is reported, separately from the call logic.

In the illustrated embodiment, interface 800 allows a user to specify logic for when various results are reported and what information to specify for reported rules. For example, if HSV Positive is not true and HSV Negative is true, "Not Detected" is returned. This may allow granularity in reporting of assay results, as well as avoiding reporting information that a patient should not see, in some embodiments.

Turning now to FIG. 8B, one embodiment of a user interface 850 usable to input graphing rules is shown. In the illustrated embodiment, interface 850 is used to control what graphs are included in a report under what circumstances (e.g., based on the call logic rules), restrict graphed ranges, and provide offsets. In various embodiments, any of various appropriate graphing rules may be specified. This may allow a user to ensure that irrelevant information for a given user-defined assay is not displayed.

Turning now to FIG. 9, one embodiment of a truth table 900 is shown. In the illustrated embodiment, truth table 900 includes columns that specify possible combinations of various assay conditions (SPC CT, SPC TM, HSV CT, HSV-2 TM, HSV-1 TM, and MC TM, in the illustrated example). In the illustrated embodiment, table 900 further indicates assay results, type, channel result, channel CTs, and channel TMs based on these combinations. Table 900 may displayed or printed and may be used by to check that call logic rules and dependencies have been specified correctly.

In some embodiments, a debug interface (not shown) may be used to debug an assay while it is being developed. In one embodiment, the debug interface shows various named structures and call logic rules and indicates whether they have been identified or satisfied. This interface may be used to determine whether parameters and/or call logic rules have been correctly specified, determine how to modify parameters and/or call logic rules to improve assay accuracy, understand additional details for a particular assay result, etc.

FIG. 10 shows an exemplary detailed report 1000 for an assay. The report indicates that the melt calibrator was passed, does not specify SPC results, and indicates that HSV 1 was detected. The report also indicates CT and TM values for HSV 1&2 and a TM value for the melt calibrator. The report also includes an amplification graph for the PCR portion of the assay and a melt graph for the melt portion of the assay. In the illustrated embodiment, the amplification graph shows that amplification occurred, while the information represented in the melt graph identifies the amplicon as an HSV-1 amplicon.

In the illustrated embodiment, the HSV 1&2 CT value of 26.0 corresponds to a point near where the amplification curve begins to deflect down from the flat portion of the line at RFU 0 while the melt temperature corresponds to the lowest dip in the melt graph. In the illustrated embodiment the HSV 1 TM value of 85.8 corresponds to the largest dip in the melt graph. In the illustrated embodiment, the MC TM value of 73.4 corresponds to the other large dip in the melt graph. In the illustrated embodiment, a delta temp of 73.4-72.0=1.4 degrees may be determined and used to adjust the x-axis of the melt graph.

In the illustrated embodiment, report 1000 also includes a cassette serial number that may be used to identify a tested sample (e.g., a label with the cassette number may be attached to each sample). In some embodiments, the cassette serial number may be used to identify an assay to run for a particular cassette. For example, assay device 220 may be configured to perform multiple different types of assays and the serial number may indicate one of the types. Further, the serial number may be used to indicate a user-modified or user-created assay that has been downloaded to assay device 220.

Exemplary Method

Figure 11:
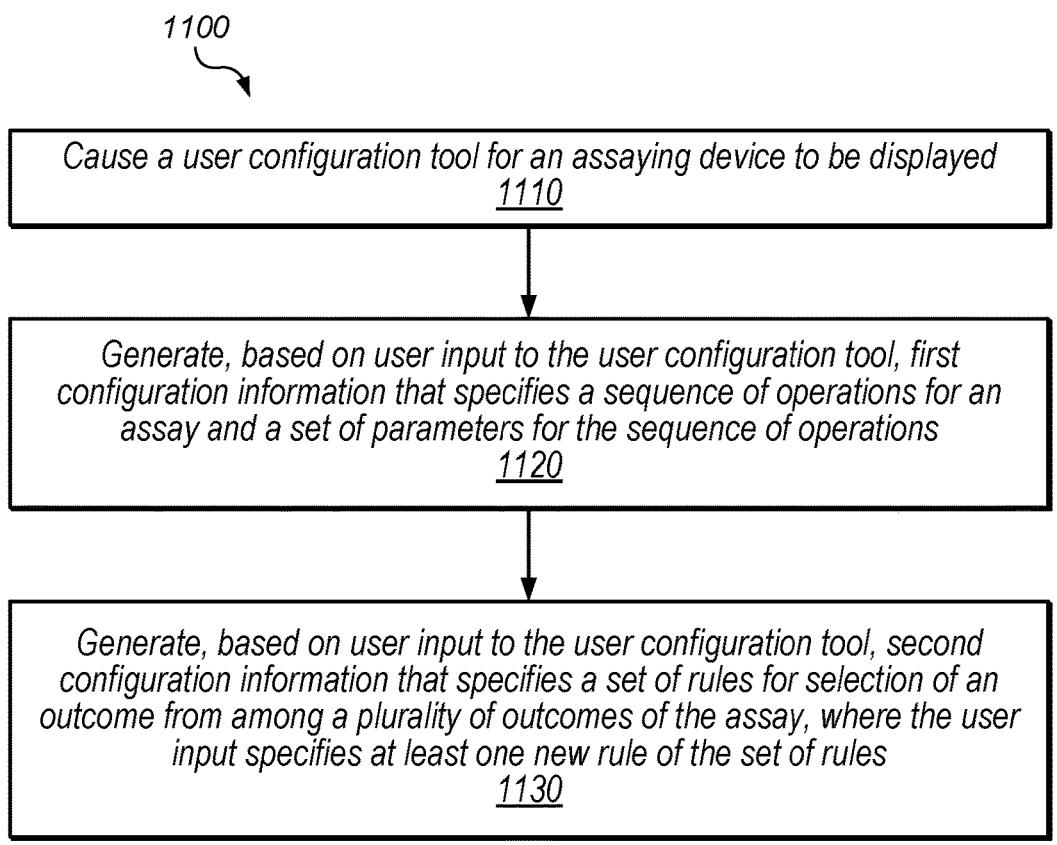
FIG. 11 is a flow diagram illustrating one embodiment of a method for configuring an assay.

FIG. 11 shows a flow diagram illustrating one exemplary embodiment of a method 1100 for configuring an assay. The method shown in FIG. 11 may be used in conjunction with any of the computer systems, devices, elements, or components disclosed herein, among other devices. In various embodiments, some of the method elements shown may be performed concurrently, in a different order than shown, or may be omitted. Additional method elements may also be performed as desired. Flow begins at step 1110.

At step 1110, a computing device (e.g., device 1210 described below with reference to FIG. 12) causes a user configuration tool for an assaying device to be displayed. In some embodiments, the user configuration tool includes graphical user interfaces, such as those shown in FIGS. 3-8. In other embodiments, the user configuration tool may be at least partially text-based. In some embodiments, the user configuration tool is displayed on a computing device that is separate and distinct from assaying device 220. Flow proceeds to step 1120.

At step 1120, the computing device generates, based on user input to the user configuration tool, first configuration information that specifies a sequence of operations for an assay and a set of parameters for the sequence of operations. In some situations, the user may generate the entirety of the first configuration information using the configuration tool. In other situations, the user configuration tool may present the user with default configuration information for the sequence of operations and/or the set of parameters, and the user may modify the default configuration information to generate the first configuration information. FIG. 4, discussed above, shows one embodiment of an interface configured to receive user input for the set of parameters. In some embodiments, the first configuration information may also include assay settings, such as those shown in FIG. 3 for example. In the embodiment of FIG. 3, the user may add a test to an assay, modify a dye used for a particular assay test, etc. In the embodiment of FIG. 4, the user may add/modify/ remove parameters, add/modify/remove assay steps (this may alternatively or additionally be performed by modifying a protocol script), etc. For the sequence of operations, the user may add/remove/modify operations using a graphical user interface and/or by modifying program instructions for the sequence. Flow proceeds to step 1130.

At step 1130, the computing device generates, based on user input to the user configuration tool, second configuration information that specifies a set of rules for selection of an outcome from among a plurality of outcomes of the assay. In the illustrated embodiment, user input specifies at least one new rule of the set of rules. For example, referring to FIG. 7, the user may use the icon at the lower right-hand portion of the figure to add a rule that was not previously present in a set of call logic rules for the assay. Further, in this embodiment, the user may add/remove/modify other rules for selecting assay outcomes. Further, in various embodiments, the user may add/remove/modify analysis parameters (which may specify signal processing functionality for raw assay data, to be performed before applying call logic rules) such as those described above with reference to FIG. 5. In some embodiments, the user may add/modify/ remove reporting rules and/or graphics rules for the assay.

Exemplary Computing Device

Figure 12:
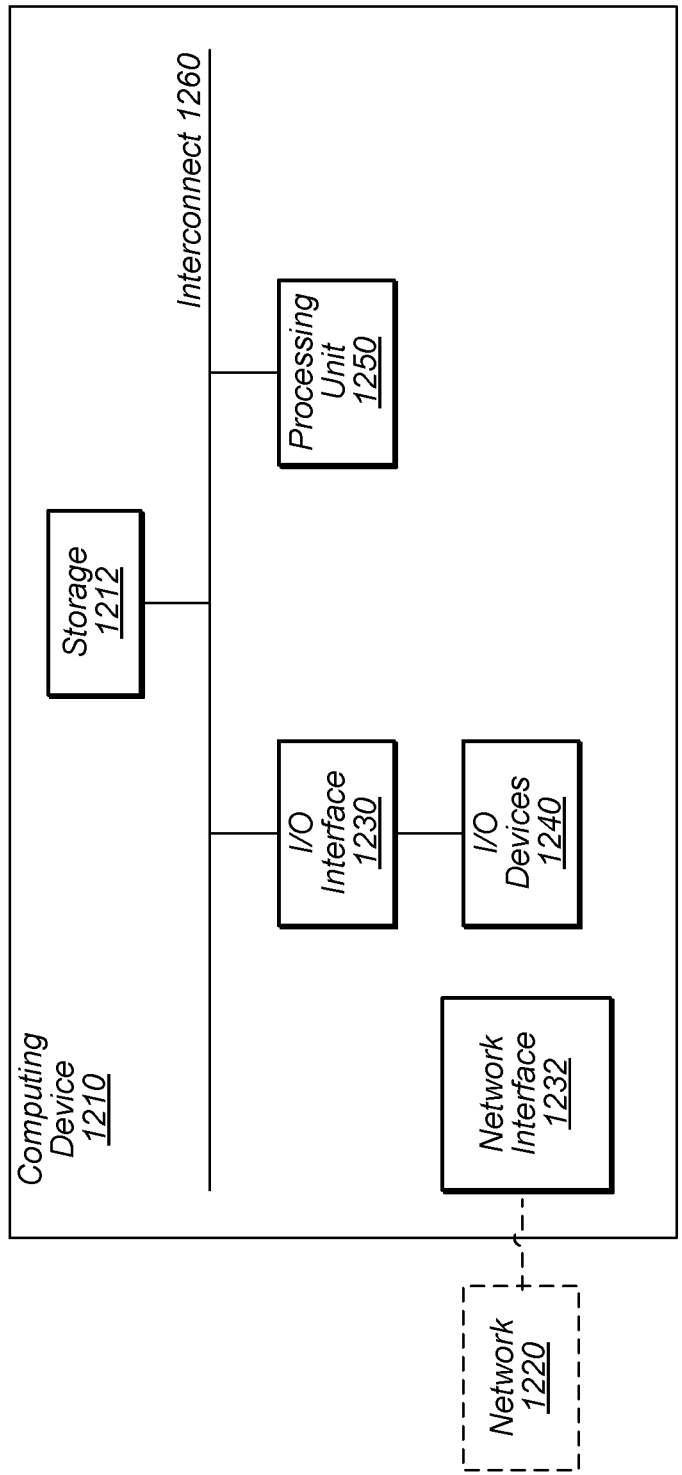
FIG. 12 shows a block diagram illustrating one embodiment of a computing device.

Turning now to FIG. 12, a block diagram of one embodiment of computing device 1210 is depicted. Computing device 1210 may be used to implement various portions of this disclosure. Computing device 1210 may be any suitable type of device, including, but not limited to, a personal computer system, desktop computer, laptop or notebook computer, mainframe computer system, web server, workstation, or network computer. As shown, computing device 1210 includes processing unit 1250, storage 1212, input/ output (I/O) interface 1230 coupled via an interconnect 1260 (e.g., a system bus). I/O interface 1230 may be coupled to one or more I/O devices 1240. Computing device 1210 further includes network interface 1232, which may be coupled to network 1220 for communications with, for example, other computing devices.

In some embodiments, computing device 1210 is a separate and distinct device from assay device 220. This may allow changes to a detailed assay specification using computing device 1210 without requiring complete re-validation of assay device 220. In some embodiments, computing device 1210 is configured to provide a user configuration tool usable to perform the assay configuration described above with reference to FIGS. 3-11. In some embodiments, the tool is used to generate and/or modify assay settings, thermal parameters, analysis parameters, call logic rules, report settings, etc. In one embodiment, this information is used to generate one or more files that are transferred to assay device 220 and/or data processing unit 230. The transfer may be performed using a wired network, wirelessly, using a physical storage medium such as a CD or USB storage device, etc. in various embodiments. In some embodiments, assay device 220 includes data processing unit 230 and is configured to perform an assay based on the one or more files. In other embodiments, computing device 1210 includes data processing unit 230 and is configured to process raw assay data generated by assay device 220, e.g., based on analysis parameters and call logic rules.

As described above, processing unit 1250 includes one or more processors. In some embodiments, processing unit 1250 includes one or more coprocessor units. In some embodiments, multiple instances of processing unit 1250 may be coupled to interconnect 1260. Processing unit 1250 (or each processor within 1250) may contain a cache or other form of on-board memory. In some embodiments, processing unit 1250 may be implemented as a general-purpose processing unit, and in other embodiments it may be implemented as a special purpose processing unit (e.g., an ASIC). In general, computing system 1210 is not limited to any particular type of processing unit or processor subsystem.

As used herein, the terms "processing unit" or "processing element" refer to circuitry configured to perform operations or to a memory having program instructions stored therein that are executable by one or more processors to perform operations. Accordingly, a processing unit may be implemented as a hardware circuit implemented in a variety of ways. The hardware circuit may include, for example, custom very-large-scale integration (VLSI) circuits or gate arrays, off-the-shelf semiconductors such as logic chips, transistors, or other discrete components. A processing unit may also be implemented in programmable hardware devices such as field programmable gate arrays, programmable array logic, programmable logic devices, or the like. A processing unit may also be configured to execute program instructions from any suitable form of non-transitory computer-readable media to perform specified operations.

Storage subsystem 1212 is usable by processing unit 1250 (e.g., to store instructions executable by and data used by processing unit 1250). Storage subsystem 1220 may be implemented by any suitable type of physical memory media, including hard disk storage, floppy disk storage, removable disk storage, flash memory, random access memory (RAM-SRAM, EDO RAM, SDRAM, DDR SDRAM, RDRAM, etc.), ROM (PROM, EEPROM, etc.), and so on. Storage subsystem 1212 may consist solely of volatile memory in one embodiment. Storage subsystem 1212 may store program instructions executable by computing device 1210 using processing unit 1250, including program instructions executable to cause computing device 1210 to implement the various techniques disclosed herein.

I/O interface 1230 may represent one or more interfaces and may be any of various types of interfaces configured to couple to and communicate with other devices, according to various embodiments. In one embodiment, I/O interface 1230 is a bridge chip from a front-side to one or more back-side buses. I/O interface 1230 may be coupled to one or more I/O devices 1240 via one or more corresponding buses or other interfaces. Examples of I/O devices include storage devices (hard disk, optical drive, removable flash drive, storage array, SAN, or an associated controller), network interface devices, user interface devices or other devices (e.g., graphics, sound, etc.).

Various articles of manufacture that store instructions (and, optionally, data) executable by a computing system to implement techniques disclosed herein are also contemplated. These articles of manufacture include non-transitory computer-readable memory media. The contemplated non-transitory computer-readable memory media include portions of a memory subsystem of a computing device as well as storage media or memory media such as magnetic media (e.g., disk) or optical media (e.g., CD, DVD, and related technologies, etc.). The non-transitory computer-readable media may be either volatile or nonvolatile memory.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method, comprising:
   receiving, at a polymerase chain reaction assaying device, test operation configuration information useable by the assaying device to cause the assaying device to perform a sequence of test operations based on a set of test operation parameters to generate data for a sample;
   receiving, at a data processing device, result processing configuration information usable by the data processing device to cause the data processing device to determine an outcome for the assay based on the data for the sample and a set of outcome identification rules specified by the result processing configuration information;
   wherein the test operation configuration information and result processing configuration information were generated by a computer system that is remote from the assaying device and the data processing device by the computer system:
      causing a user configuration tool for the assaying device to be displayed;
      receiving, from a user via the user configuration tool, test operation input that indicates an assay to be performed;
      generating, based on the test operation input, the test operation configuration information that specifies the sequence of test operations for the assay to be performed by the assaying device and specifies the set of test operation parameters for the sequence of test operations;
      receiving, from the user, outcome identification input that specifies at least one rule for identification of an outcome from among a plurality of potential outcomes; and
      generating, based on the outcome identification input, the result processing configuration information that specifies the set of outcome identification rules for identification of an outcome from among a plurality of potential outcomes of the assay
   performing, by the assaying device, the sequence of test operations based on the set of test operation parameters to generate data for the sample; and
   processing, by the data processing device, the data based on the set of outcome identification rules to generate an outcome for the assay.

2. The method of claim 1, wherein the data is fluorescence data.

3. The method of claim 1, wherein generating the result processing configuration information is based on one or more user-specified logical dependencies between outcome identification rules of the set of outcome identification rules.

4. The method of claim 1, further comprising:
   performing signal processing operations on the data based on analysis parameters included in the result processing configuration information to generate processed data.

5. The method of claim 1, wherein the set of outcome identification rules includes a particular outcome identification rule related to detecting a cycle threshold or a melting temperature.

6. A system comprising:
   a polymerase chain reaction (PCR) assaying device useable to perform an assay;
   a data processing device; and
   one or more memories storing:
      test operation configuration information useable by the assaying device to cause the assaying device to perform a sequence of test operations based on a set of test operation parameters to generate data for a sample;
      result processing configuration information usable by the data processing device to cause the data processing device to determine an outcome for the assay based on the data for the sample and a set of outcome identification rules specified by the result processing configuration information; and
      instructions that when executed by the system cause the system to receive the test operation configuration information and result processing configuration information;
      wherein the test operation configuration information and result processing configuration information were generated by:
         receiving, from a user, test operation input that indicates the assay to be performed;
         generating, based on the test operation input, the test operation configuration information that specifies the sequence of test operations for the assay to be performed by the assaying device and specifies the set of test operation parameters for the sequence of test operations;
         receiving, from the user, outcome identification input that specifies at least one rule for identification of an outcome from among a plurality of potential outcomes; and
         generating, based on the outcome identification input, the result processing configuration information that specifies the set of outcome identification rules for identification of an outcome from among a plurality of potential outcomes of the assay based on results of the sequence of test operations.

7. The system of claim 6, wherein the data is fluorescence data.

8. The system of claim 6, wherein the test operation configuration information and result processing configuration information were generated by:
   presenting a user configuration tool for the assaying device; and wherein the test operation configuration information and outcome identification input a received via the user configuration tool.

9. The system of claim 6, wherein the test operation configuration information and the result processing configuration information were generated by a remote computing device.

10. The system of claim 6, wherein the set of outcome identification rules includes a particular outcome identification rule related to detecting a cycle threshold or a melting temperature.

* * * * *